United States Patent [19]

Photis

[11] 4,316,859
[45] Feb. 23, 1982

[54] PREPARATION OF ARYLPHOSPHINIC ACIDS

[75] Inventor: James M. Photis, Ridgefield, Conn.

[73] Assignee: Stauffer Chemical Company, Westport, Conn.

[21] Appl. No.: 248,103

[22] Filed: Mar. 27, 1981

[51] Int. Cl.$^3$ .............................................. C07F 9/28
[52] U.S. Cl. ............................................ 260/502.4 R
[58] Field of Search ................................ 260/502.4 R

[56] References Cited

U.S. PATENT DOCUMENTS

| 2,137,792 | 11/1938 | Woodstock | 260/502.4 R |
|---|---|---|---|
| 2,594,454 | 4/1952 | Kosolapoff | 260/502.4 R |
| 2,632,018 | 3/1953 | Kosolapoff | 260/502.4 R |
| 3,903,208 | 9/1975 | Hofer et al. | 260/502.4 R |
| 3,974,217 | 8/1976 | Miles | 260/543 P |

OTHER PUBLICATIONS

Higgins et al., "J. Am. Chem. Soc.",vol. 77 (1955), pp. 1864–1866.
Frank, "Chemical Reviews", vol. 61 (1961), pp. 389–424.
Kosolapoff, "Organophosphorus Compounds", pp. 43–46 and 128.

*Primary Examiner*—Joseph E. Evans
*Attorney, Agent, or Firm*—William C. Gerstenzang

[57] ABSTRACT

Arylphosphinic acids are prepared by reacting an aryl compound with phosphorus trichloride in the presence of aluminum trichloride to form a first reaction product, adding the first reaction product to water to precipitate a second reaction product and then treating the second reaction product sequentially with a halogenating agent and with water to form the arylphosphinic acid.

8 Claims, No Drawings

PREPARATION OF ARYLPHOSPHINIC ACIDS

BACKGROUND OF THE INVENTION

The present invention relates to an improved process for the preparation of arylphosphinic acids. More particularly, the present invention relates to a process for preparing arylphosphinic acids by an aluminum chloride catalyzed reaction of an aryl compound with phosphorus trichloride in which the prior art difficulties associated with separating the product from aluminum chloride complexes are effectively solved.

Arylphosphinic acids are compounds which are useful as catalysts and stabilizers in nylon synthesis and are also useful as intermediates in the production of a wide variety of useful compositions, such as pesticides, fuel and oil additives and the like.

One of the best known methods for preparing these compounds involves the reaction of an aryl compound with phosphorus trichloride in the presence of aluminum trichloride to produce an aryl phosphonous dichloride, which is then hydrolyzed to produce the acid. Unfortunately, however, the aluminum chloride forms certain complexes during the process, which makes recovery of the final product difficult.

A method suggested by the prior art for circumventing the problems presented by the aluminum chloride complexes involves the addition of phosphorus oxychloride to the reaction mixture to form an aluminum chloride-phosphorus oxychloride complex, which settles out of the reaction mixture, thereby facilitating recovery of the aryl phosphonous dichloride product. While this method is helpful, it is less than desirable because large amounts of phosphorus oxychloride are required and the remaining aluminum chloride-phosphorus oxychloride precipitate is a reactive waste product which can be difficult to dispose of. In addition, not all of the aluminum complex is removed, and the small amount remaining can lead to the formation of an emulsion during a subsequent reaction of the aryl phosphonous dichloride with water, which further complicates the process.

U.S. Pat. No. 3,974,217 teaches the preparation of alkoxy and alkylthio substituted phenyl phosphonous dichlorides by reacting an appropriate substituted aryl compound with phosphorus trichloride in the presence of stannic chloride or titanium tetrachloride. It would appear, however, that this method would be less than successful with compounds not having the activating alkoxy or alkylthio substituents, since the catalysts used are less effective Friedel-Crafts catalysts.

A need therefore exists for a method by which arylphosphinic acid esters can be prepared from appropriate aryl compounds and phosphorus trichloride using aluminum chloride as catalyst without encountering the prior art difficulties occasioned by the formation of aluminum chloride complexes.

SUMMARY OF THE INVENTION

It has now been found that arylphosphinic acids can be prepared from appropriate aryl compounds and phosphorus trichloride, using aluminum chloride catalyst, without encountering the prior art difficulties occasioned by the presence of aluminum chloride complexes by adding the initial reaction product to water to form a precipitate which can then be treated with a halogenating agent and then with water to form the desired arylphosphinic acid.

DETAILED DESCRIPTION OF THE INVENTION

In accordance with the present invention there is provided a process for the preparation of arylphosphinic acids comprising reacting an aryl compound susceptible to electrophilic ring substitution with phosphorus trichloride in the presence of aluminum chloride to form a first reaction product, adding the first reaction product to water to precipitate a second reaction product, recovering said precipitate and sequentially reacting it with a halogenating agent and with water to form an arylphosphinic acid.

The aryl compounds which are used in the practice of the present invention are those which are susceptible to electrophilic ring substitution. They include, but are not limited to compounds represented by the formula:

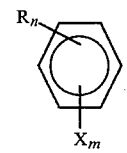

wherein each R is independently hydrogen, alkyl having from 1 to about 12 carbon atoms, alkoxy having from 1 to about 6 carbon atoms, alkylthio having from 1 to about 6 carbon atoms, aryl or substituted aryl having from 6 to about 12 carbon atoms or cycloalkyl having from 3 to about 8 carbon atoms; n represents a number ranging from 0 to 5; X represents hydrogen or a halogen and m represents a number ranging from 0 to 5. Preferred aryl compounds are those wherein R is alkyl or alkoxy having from 0 to about 4 carbon atoms.

Exemplary aryl compounds include benzene, toluene, naphthalene, p-xylene, p-chlorotoluene, 1,3,5-trimethylbenzene and biphenyl.

Heterocyclic compounds, such as thiophene can be used in place of the aryl compound, and compounds having more than one benzene ring such as diphenylmethane and polyphenyl ethers can also be used.

A particular preferred aryl compound is p-xylene.

The reaction between the aryl compound and $PCl_3$ is preferably carried out in an excess of phosphorus trichloride. The amount of phosphorus trichloride charged therefore ranges from about 1 to about 5 moles per mole of aryl compound charged, and preferably from about 2 to about 4 moles phosphorus trichloride per mole aryl compound.

It is also preferred to use relatively large amounts of the aluminum chloride catalyst. The amount of aluminum chloride charged therefore ranges from about 1 mole aluminum chloride per mole aryl compound to about 5 moles aluminum chloride per mole aryl compound, although a range of from about 1 to about 1.5 moles aluminum chloride per mole aryl compound is preferred. The process is operable at lower or higher catalyst ratios, but with lower catalyst ratios conversion to the desired product may not be as complete as desired, while with higher ratios unwanted by-products resulting from multiple substitution on phosphorus could result.

The halogenating agents which are used in the practice of the present invention include, but are not limited to $PCl_3$, $PCl_5$, $POCl_3$, $Cl_2$, $SOCl_2$, $SO_2Cl_2$ and the like;

although PCl₃ is preferred. The amount of halogenating agent charged ranges from about 1 to about 3 moles per mole of aryl compound charged.

The temperature at which the various stages of the process are carried out will vary in accordance with many conditions, such as the amount of catalyst used, the particular aryl compound being used and the like. The initial reaction between the aryl compound and phosphorus trichloride is generally conducted at a temperature ranging from about 20° C. to about 100° C. or higher, although a temperature ranging from about 50° C. to about 75° C. is preferred. The subsequent reaction of the first reaction product with water can be conducted at room temperature or at an elevated temperature, but a reduced temperature (i.e., between about 0° C. and about 20° C.) is preferred. Reaction of the precipitate with the halogenating agent and water is generally conducted at ambient temperature, although higher or lower temperatures can also be used.

In practicing the present invention the aryl compound and PCl₃ are reacted in the presence of aluminum chloride in the same manner as has been practiced in the prior art. Thus, the reactants are mixed together in appropriate ratios, with the PCl₃ and, in many cases, the aryl compound, serving the dual role of reactant and solvent. The reaction tends to be somewhat slow at ambient temperatures and it is therefore preferable to heat the reaction mixture so that a reasonable reaction rate can be achieved. It is preferred to conduct the reaction at a temperature of about 50°–75° C. and with provision for treatment of hydrogen chloride gas which is released during the process.

The reaction product is then stripped of volatile components, which include excess PCl₃, and poured into water which reacts with the first reaction product to form a second reaction product as a precipitate. This reaction is exothermic and it is therefore preferable that the water be at a reduced temperature and that external cooling be provided.

It is important that the first reaction product be poured into water rather than the reverse. Should water be added to the reaction product rather than the reaction product added to the water, the ultimate results achieved will not be as successful.

The precipitate which is formed in then isolated and added to an inert media to form a slurry. Suitable media include, but are not limited to methylene chloride, ethylene dichloride, toluene and the like; with the halogenated media being preferred because the ultimate arylphosphinic acids being prepared are generally soluble in such media.

Phosphorus trichloride is then added to the slurry and the slurry heated, preferably to reflux temperature, for a time sufficient to complete the evolution of hydrogen chloride gas. The slurry is then cooled and water added slowly, to form the arylphosphinic acid. The amount of water used generally ranges from about 1 to about 10 moles per mole of aryl compound charged initially, although greater amounts can be used without harm. The final product can then be worked up by standard techniques.

In order that the present invention be more fully understood, the following example is given by way of illustration. No specific details or enumerations contained therein should be construed as limitations to the present invention except insofar as they appear in the appended claims. All parts and percentages are by weight unless otherwise specifically designated.

EXAMPLE

PREPARATION OF 2,5-DIMETHYLPHENYLPHOSPHINIC ACID

To a mechanically stirred solution of 280 ml. (242 g., 2.3 moles) of p-xylene and 675 ml. (1070 g., 7.8 moles) of phosphorus trichloride was added 400 g. (3.0 moles) of anhydrous aluminum chloride all at once. The reaction mixture was heated at 70°–75° C. for 2.5–3.5 hours. Volatile components (PCl₃/p-xylene) were removed under reduced pressure. The resulting amber colored syrup was slowly poured into 3.5 liters of cold water with stirring. An insoluble, granular, white solid formed which was isolated by suction filtration. The solid was washed with water and allowed to air dry; yield 282–290 g. A mechanically stirred slurry of the solid and 1 liter of ethylene dichloride was treated slowly at ambient temperature with 250 ml. of the PCl₃/p-xylene volatile fraction from above. After the addition the reaction was heated at reflux for 15 minutes. After cooling, 200 ml. of water was introduced dropwise. All solids dissolved. The lower aqueous layer was removed and the organic layer was washed once with concentrated hydrochloric acid. The organic layer was then mixed with two volumes of water. With stirring, solid sodium bicarbonate was introduced until the evolution of CO₂ ceased. The organic layer was removed and discarded. The aqueous layer was made strongly acidic with concentrated hydrochloric acid. The pale yellow oil which separated was extracted with methylene chloride. The methylene chloride extract was dried over magnesium sulfate and filtered. Evaporation of the solvent afforded 174 g. of 2,5-dimethylphenylphosphinic acid which completely solidified upon standing, m.p. 73°–80° C.

Analysis: Theory: Calculated for $C_8H_{11}O_2P$; P, 18.2 Found: P, 17.7.

I claim:

1. A process for the preparation of arylphosphinic acids comprising reacting an aryl compound susceptible to electrophilic ring substitution with phosphorus trichloride in the presence of aluminum chloride to form a first reaction product, adding said first reaction product to water to precipitate a second reaction product, recovering said precipitate and sequentially treating it with a halogenating agent and with water to form an arylphosphinic acid.

2. The process of claim 1 wherein said aryl compound is an aryl compound represented by the structure

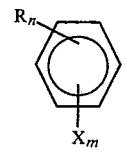

wherein each R is independently hydrogen, alkyl having from 1 to about 12 carbon atoms, alkoxy having from 1 to about 6 carbon atoms, aryl or substituted aryl having from 6 to about 12 carbon atoms or cycloalkyl having from 3 to about 8 carbon atoms; X represents hydrogen or a halogen, n represents a number ranging from 0 to 5 and m represents a number ranging from 0 to 5.

3. The process of claim 2 wherein said aryl compound is a compound selected from the group consisting of benzene, naphthalene, p-xylene, p-chlorotoluene, 1,3,5-trimethyl benzene and biphenyl.

4. The process of claim 3 wherein said aryl compound is p-xylene.

5. The process of claim 1 wherein the amount of $PCl_3$ present during the reaction between said aryl compound and $PCl_3$ ranges from 1 to about 5 moles $PCl_3$ per mole aryl compound.

6. The process of claim 5 wherein the amount of aluminum chloride present during said reaction between said aryl compound and said $PCl_3$ ranges from 1 to about 5 moles aluminum chloride per mole aryl compound.

7. The process of claim 1 wherein said halogenating agent is selected from the group consisting of $PCl_3$, $POCl_3$, and $SOCl_2$.

8. The process of claim 7 wherein said halogenating agent is $PCl_3$.

* * * * *